(12) United States Patent
Abrams et al.

(10) Patent No.: US 7,128,736 B1
(45) Date of Patent: Oct. 31, 2006

(54) DETACHABLE ANEURYSM NECK CLOSURE PATCH

(75) Inventors: Robert M. Abrams, Sunnyvale, CA (US); Erik T. Engelson, Menlo Park, CA (US); John B. Pedersen, Danville, CA (US); Harold F. Carrison, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 09/548,644

(22) Filed: Apr. 13, 2000

Related U.S. Application Data

(63) Continuation of application No. 09/148,411, filed on Sep. 4, 1998, now abandoned.

(51) Int. Cl.
*A61B 17/00* (2006.01)

(52) U.S. Cl. .......................... 606/1; 606/108; 606/191; 606/213

(58) Field of Classification Search .................... 606/1, 606/108, 191, 213
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 4,710,192 A | 12/1987 | Liotta et al. | |
| 4,739,768 A | 4/1988 | Engelson | |
| 4,994,069 A | 2/1991 | Ritchart et al. | |
| 5,122,136 A | 6/1992 | Guglielmi et al. | |
| 5,226,911 A | 7/1993 | Chee et al. | |
| 5,250,071 A | 10/1993 | Palermo | |
| 5,261,916 A | 11/1993 | Engelson | |
| 5,354,295 A | 10/1994 | Guglielmi et al. | |
| 5,397,331 A | 3/1995 | Himpens et al. | |
| 5,527,338 A | 6/1996 | Purdy | |
| 5,624,449 A | 4/1997 | Pham et al. | |
| 5,693,067 A | 12/1997 | Purdy | |
| 5,718,711 A | 2/1998 | Berenstein et al. | |
| 5,733,294 A | 3/1998 | Forber et al. | |
| 6,063,070 A * | 5/2000 | Eder ......................... | 606/213 |
| 2002/0143349 A1 | 10/2002 | Gifford, III et al. | |

FOREIGN PATENT DOCUMENTS

| | | |
|---|---|---|
| EP | 0 820 726 A2 | 1/1998 |
| WO | WO 97/26939 A1 | 7/1997 |
| WO | WO 97/31672 A1 | 9/1997 |
| WO | WO 99/05977 A1 | 2/1999 |
| WO | WO 99/07294 A1 | 2/1999 |
| WO | WO 00/13593 | 3/2000 |

\* cited by examiner

*Primary Examiner*—Lee S. Cohen
(74) *Attorney, Agent, or Firm*—Vista IP Law Group LLP

(57) ABSTRACT

This is a device for bridging the neck of either an aneurysm in the vasculature and stabilizing the presence of vaso-occlusive devices (such as helically wound coils) in that aneurysm. The closure patch may be delivered either from the exterior of the distal end of a catheter or delivered from the catheter lumen. It is preferably implanted by the severance of an included electrolytically severable joint. The retainer assembly itself typically has a number of radially projecting elements which are, in turn, attached to a scrim-like fabric, preferably collagen-coated Dacron, extending among the various radially projecting elements. The closure patch is intended to be resident within the aneurysm after it is deployed. After deployment, the aneurysm may be at least partially filled with vaso-occlusive devices such as helically wound coils.

11 Claims, 4 Drawing Sheets

DETACHABLE ANEURYSM NECK CLOSURE PATCH

CROSS-REFERENCE TO RELATED APPLICATIONS

This application is a continuation of U.S. patent application Ser. No. 09/148,411 filed Sep. 4, 1998, now abandoned.

FIELD OF THE INVENTION

This invention is a device for bridging the neck of either an aneurysm in the vasculature and stabilizing the presence of vaso-occlusive devices (such as helically wound coils) in that aneurysm. The patch may be ccombined with a component residing within the aneurym for providing form to the aneurysm or for anchoring the assembly to the aneurysm. The closure patch may be delivered either from the exterior of the distal end of a catheter or delivered from the catheter lumen. It is preferably implanted by the severance of an included electrolytically severable joint. The retainer assembly itself typically has a number of generally radially projecting elements which are, in turn, attached to a scrim-like fabric extending among the various radially projecting elements. The closure patch may be resident within the aneurysm after it is deployed or in the exterior vessel. After deployment, the aneurysm may be at least partially filled with vaso-occlusive devices such as helically wound coils.

BACKGROUND OF THE INVENTION

Different implantable medical devices have been developed for treating a number of ailments associated with body lumens. In particular, occlusive devices are useful in filling vascular or other body spaces. Some body spaces, such as vascular aneurysms, are formed due to a weakening in artery walls. Often these aneurysms are the site of internal bleeding and stroke. A variety of different embolic agents are known as, at least arguably, suitable for treatment of these anomalies. These treatments are commonly known as "artificial vaso-occlusion."

One such class of embolic agents includes injectable fluids or suspensions, such as microfibrillar collagen, various polymeric beads, and polyvinylalcohol foam. These polymeric agents may additionally be crosslinked, sometimes in vivo, to extend the persistence of the agent at the vascular site. These agents are often introduced into the vasculature through a catheter. After such introduction, the introduced materials there form a solid space-filling mass. Although some provide excellent short-term occlusion, many are thought to allow vessel recanalization due to absorption of polymer into the blood. Another procedure in which a partially hydrolyzed polyvinylacetate (PVA) is dissolved in an ethanol solvent and ejected into a desired vascular site is found in Park et al. U.S. patent application Ser. No. 08/734,442 filed Oct. 17, 1996 for "LIQUID EMBOLIC AGENTS". Other materials such as hog hair and suspensions of metal particles have also been suggested and used by those wishing to form occlusions.

Other materials including polymer resins, typically cyanoacrylates, are also employed as injectable vaso-occlusive materials. These resins are typically mixed with an ionic radio-opaque contrast material or are made radio-opaque by the addition of a tantalum powder. Their use is fraught with problems in that placement of the mixture is quite difficult. These materials may crosslink with the human body. Inadvertent embolisms in normal vasculature (due to difficulty in controlling the destination of the resins) are not uncommon. The material is also difficult or impossible to retrieve once it has been placed in the vasculature.

Over the past few years, advancements in the artificial occlusion of vessels and aneurysms have included the delivery and implantation of metal coils as vaso-occlusive devices. Implantable metal coils that are useful as artificial occlusion devices in vasculature lumens or aneurysms are herein referred to as "vaso-occlusive coils."

Vaso-occlusion coils are generally constructed of a wire, usually made of a metal or metal alloy, that is wound into a helix. Many such devices are introduced to the selected target site through a catheter in a stretched or linear form. The vaso-occlusive device assumes an irregular shape upon discharge of the device from the distal end of the catheter a variety of vaso-occlusive coils and braids are known. For instance, U.S. Pat. No. 4,994,069, to Ritchart et al., shows a flexible, preferably coiled, wire for use in small vessel vaso-occlusion. Unlike vaso-occlusive coils used prior to that time, Ritchart et al taught a coil which is fairly soft and is delivered to the site using a pusher within a catheter lumen. Upon discharge from the delivery catheter, the coil may undertake any of the number of random or regular configurations used to fill the site. The coils may be used for small vessel sites, e.g., 0.5–6 mm in diameter. The coils themselves are described as being between 0.010 and 0.030 inches in diameter. The length of the coil wire is typically 15 to 20 times the diameter of the vessel to be occluded. The wire used to make up the coils may be, for instance, 0.002 to 0.006 inches in diameter. Tungsten, platinum, and gold threads or wires are said to be preferred. These coils have a variety of benefits including the fact that they are relatively permanent, they may be easily imaged radiographically, they may be located at a well-defined vessel site, and they can be retrieved.

It is common that these vaso-occlusive devices be delivered through microcatheters such as the type disclosed in U.S. Pat. No. 4,739,768, to Engelson. These microcatheters track a guidewire to a point just proximal or within the desired site for occlusion. The coil is advanced through the microcatheter (once the guidewire is removed) and out the distal end hole so to at least partially fill the selected space and create an occlusion.

In addition to vaso-occlusion devices or coils having predetermined secondary shapes that dictate in part their space filling mechanism, other vaso-occlusive coils have been disclosed that take on random shapes when expelled from a delivery sheath. One such type is a vaso-occlusive coil often referred to as "a liquid coil". One example of such a vaso-occlusive coil is disclosed in U.S. Pat. No. 5,718,711, to Berenstein et al. This describes a very soft and flexible coil, which is flow-injectable through a delivery catheter using, e.g., saline solution.

In addition to the various types of space filling mechanisms and geometries of vaso-occlusive coils, other particularized features of coil designs, such as mechanisms for delivering vaso-occlusive coils through delivery catheters and implanting them in a desired occlusion site, have also been described. The examples of categories of vaso-occlusive coils based upon their delivery mechanisms include pushable coils, mechanically detachable coils, and electrolytically detachable coils.

One example of the type of vaso-occlusive coil referred to above as the "pushable coil" is disclosed in Ritchart et al., discussed above. Pushable coils are commonly provided in a cartridge and are pushed or "plunged" from the cartridge into a delivery catheter lumen. A pusher advances the pushable coil through and out of the delivery catheter lumen and into the site for occlusion.

Mechanically detachable vaso-occlusive devices are typically integrated with a pusher rod and are mechanically detached from the distal end of that pusher after exiting a delivery catheter. Examples of such mechanically detachable vaso-occlusive coils are found in U.S. Pat. No. 5,261,916, to Engelson, or U.S. Pat. No. 5,250,071, to Palermo.

Finally, examples of electrolytically detachable vaso-occlusive devices may be found in U.S. Pat. Nos. 5,122,136 and 5,354,295, each to Guglielmi et al. In these devices, the vaso-occlusive portion of the assembly is attached to a pusher via a small, electrolytically severable joint. The electrolytically severable joint is severed by the placement of an appropriate voltage on the core wire. The joint erodes in preference either to the vaso-occlusive device itself or to the pusher core wire. The core wire is often simply insulated to prevent the electrolytic response caused by the imposition of electrical current.

Further improvement upon the electrolytic detachment mechanism described just is found in U.S. patent application Ser. No. 08/205,512, filed Mar. 3, 1994, for "IMPLANT DETACHMENT DETECTION SYSTEM AND METHOD FOR DETECTING SEPARATION OF VASO-OCCLUSIVE DEVICES". This document described a procedure for superimposing a modest alternating current upon the direct current signal. A sensing circuit monitors the alternating current as an indicator of the progression of coil detachment.

Improvements in enhancing the thrombogenic or other occlusive tissue response to metal coils has also been disclosed. For example, vaso-occlusive coils having fibers attached thereto are known—see, for example, U.S. Pat. No. 5,226,911, to Chee et al.

Each of the devices described above may be used in the treatment by occlusion of aneurysms. As noted above, aneurysms present particularly acute medical risk due to the dangers of potential rupture of the thin wall inherent in such aneurysm. Occlusion of aneurysms by use of vaso-occlusive coils without occluding the adjacent artery is a special challenge and is a desirable method of reducing such risk of rupture.

As noted above, the use of vaso-occlusive coils in treating aneurysms is widespread. These vaso-occlusive devices are placed in an aneurysm in the following fashion. A microcatheter is initially steered into or adjacent to the entrance of an aneurysm, typically aided by the use of a steerable guidewire. The wire is then withdrawn from the microcatheter lumen and replaced by the vaso-occlusive coil. The vaso-occlusive coil is advanced through and out of the microcatheter, desirably being completely delivered into the aneurysm. After, or perhaps, during, delivery of such a coil into the aneurysm, there is a specific risk that a portion of the coil might migrate out of the aneurysm entrance zone and into the feeding vessel. The presence of such a coil in that feeding vessel may cause the highly undesirable response of causing an occlusion there. Also, there is a quantifiable risk that the blood flow in the vessel and aneurysm may induce movement of the coil farther out of the aneurysm, resulting in a more developed embolus in the patent vessel.

One type of aneurysm, commonly known as a "wide neck aneurysm" is known to present particular difficulty in the placement and retention of vaso-occlusive coils. Wide neck aneurysms are herein referred to as aneurysms of vessel walls having a neck or a "entrance zone" from the adjacent vessel, which entrance zone has a diameter that either: (1) is at least 80% of the largest diameter of the aneurysm; or (2) is clinically observed to be too wide effectively to retain vaso-occlusive coils that are deployed using the techniques discussed above.

Furthermore, vaso-occlusive coils lacking substantial secondary shape strength may be difficult to maintain in position within an aneurysm no matter how skillfully they are placed.

There are few disclosed devices for maintaining the presence of vaso-occlusive coils within an aneurysm. One such device is shown in U.S. patent application Ser. No. 08/690,183, filed Jul. 26, 1996, for "ANEURYSM CLOSURE DEVICE ASSEMBLY". That application describes devices that are said to be placed within the lumen of a feed vessel exterior to the aneurysm so to retain coils within the aneurysm cavity. That is to say that the retainer device is released in the good vessel exterior to the aneurysm. The device is held in place via the use of radial pressure on the vessel wall. After the device is released and set in an appropriate place, a microcatheter is inserted into the lumen behind the retainer device; the distal end of the catheter is inserted into the aneurysm cavity. One or more vaso-occlusive devices is introduced into the aneurysm cavity. The retainer device maintains the presence of those vaso-occlusive devices within the aneurysm no matter whether the aneurysm is a large mouth aneurysm or not.

Another device for closing an aneurysm is found in U.S. patent application Ser. No. 08/588,195 filed Jan. 18, 1996, for "ANEURYSM CLOSURE METHOD". In this procedure, a vaso-occlusive device such as a coil or braid has on its outer surface a polymeric composition that may be reformed or solidified in situ within the human body. The device is simply inserted into the aneurysm and the polymer is then reformed, e.g., by the application of light to melt or otherwise reform the polymer exterior to the vaso-occlusive device. The vaso-occlusive device then sticks to itself at the various sites of self-contact and forms a rigid whole mass within the aneurysm.

There are a variety of other vaso-occlusive coils and devices, which may be specified herein. The material provided above is only exemplary of the patents and publications dealing with such devices. No coil retainer device of the structure described herein is seen in any of the references described above.

SUMMARY OF THE INVENTION

This invention includes an implantable medical device useful for retaining other occlusion device at an occlusion site, such as an aneurysm, and related methods of introducing and installing that implantable retainer at the occlusion site. Combinations of the retainer device and its included vaso-occlusive material or device are also an aspect of the invention as are combinations of the retainer device and its delivery components. In particular, the invention involves an implantable retainer, which is deliverable through an elongated tubular delivery device such as a vascular catheter. The assemblage includes an implantable retainer which is placed just inside or just outside the aneurysm mouth and allowed to remain at that aneurysm mouth. The assembly includes a tubular delivery member to which it is attached by an electrolytically severable joint. In general, the implantable retainer component may either be mounted upon and extend from the distal end of the tubular delivery member or may be delivered from the lumen of the delivery.

The joint itself is desirably an electrolytically severable upon application of a suitable current to the joint, typically by use of a conductor wire which may be placed in the wall of the delivery member. The joint is comparatively more electrolytically dissolvable or erodible when a current is applied than are any of the rest of the components that surround or deliver it. The aneurysm patch itself typically includes a number of radially extending elements shaped to support a soft fabric generally attached to the radial elements. The radial elements have a primary shape during delivery, e.g., when inside the delivery tubular member, and then assume a secondary shape upon exit from the distal end of that delivery tubular member. Once the aneurysm patch subassembly containing the array elements is in place, the vaso-occlusive device, e.g. vaso-occlusive coils, may be introduced into the aneurysm either through the small tubular member to which the array members are attached or, if the array members do not have a mesh covering, through the open area found at the neck of the aneurysm.

DESCRIPTION OF THE INVENTION

This invention relates to a device and a procedure for stabilizing the position and, usually, the structure of vaso-occlusive devices which are placed in a target occlusion site, usually an aneurysm. The retaining devices or patches prevent the potential migration of those one or more occlusive devices (e.g., helically wound coils) from that target occlusion site, by forming a barrier at the entrance zone to the aneurysm where it meets a feeding vessel.

Figure 1A:
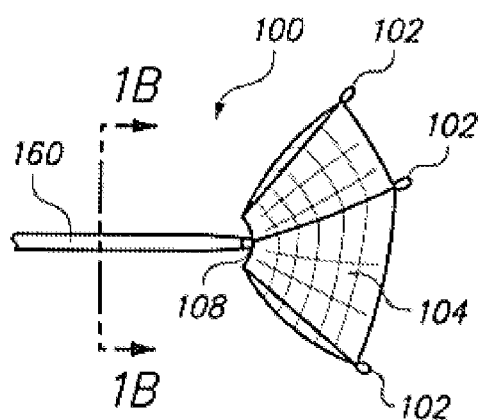
FIG. 1A shows partial side view of an aneurysm patch deliverable through a delivery catheter, all made in accordance with the invention.

FIG. 1A shows in side view one variation of an aneurysm patch (100) made according to this invention. Specifically, FIG. 1A shows an aneurysm patch (100) having a number of radially extending members (102), which may have blunted tips to prevent trauma to the arteries in which they are placed. A slight bend may be noticed in the radially extending members (102). This bend helps release the aneurysm patch (100) from the delivery catheter upon deployment. As will be shown below in more detail, the radially extending members (102) have a first or folded position along the pusher wire (106) during delivery and a second position extended as shown in FIGS. 1A and 1B after deployment.

Figure 1B:
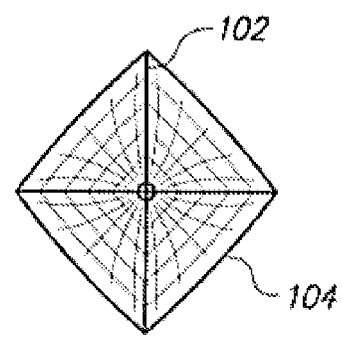
FIG. 1B shows an end view of the device depicted in FIG. 1A.

Between the radially extending members (102) in FIGS. 1A and 1B, may be seen a fabric (104). The fabric (104) is affixed to the radially extending members (102) and functions upon deployment to hold the chosen vaso-occlusive members in the aneurysm and to stabilize them in their general position in the aneurysm. Ideally, the fabric (104) is a material which promotes angiogenesis. Generally, materials useful as vascular graft materials are suitable as fabric (104) and may include, e.g., Dacron (polyethyleneterephthalate) or collageneous materials or polyluorocarbons or combinations. Thrombogenic materials are not desirable, at least during the process of introducing the device into the body. The fabric (104) ideally and ultimately forms a smooth surface in the extant surface which is not a source for production of thrombi. Other fibrous materials which may be suitable, e.g., polyglycolic acid, wool, cotton, etc. Antithrombotic agents may be added if necessary.

The radially extending members (102) are joined to the pusher wire (106) with a releasable joint (108), desirably an electrolytically severable joint made in accord, for instance, with the Guglielmi et al patents discussed elsewhere herein. It may be noticed that the radially extending members (102) form a recess at the releasable joint (108). The recess is optional but serves to prevent any stub that may remain after detachment from extending into the vessel lumen and causing a thrombus in an undesired region. The releasable joint (108) may located generally centrally on the devcie but, obviously, it is not a requirement that the joint (108) be so centered. It may be off-centered but in any event forms the situs for the detachable joint.

Figure 2A:
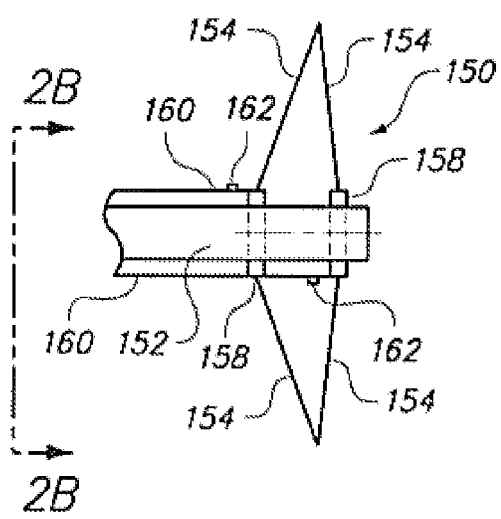
FIG. 2A shows partial side view of an aneurysm patch deliverable upon a delivery catheter, all made in accordance with the invention.
Figure 2B:
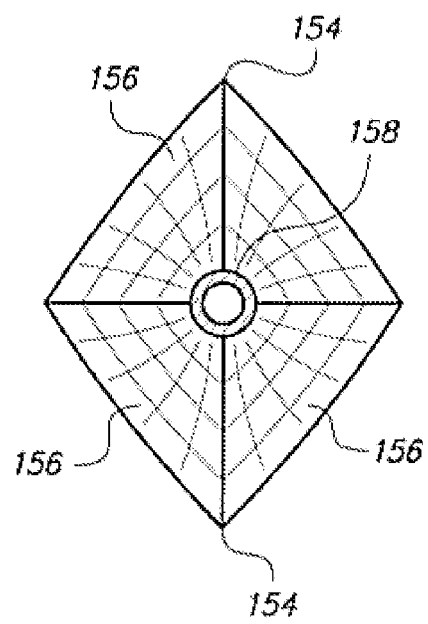
FIG. 2B shows an end view of the device depicted in FIG. 2A.

FIGS. 2A and 2B show another variation of the inventive aneurysm patch (150) that is delivered on the exterior of a tubular member or a catheter (152). This variation includes a number of radially extending members (154) which are joined at their outer ends. The radially extending members (154) are also joined by a soft fabric (156) which also may be scrim-like. The radially extending members (154) are joined to a pair of collars (158) that slide on the delivery catheter (152) and are controlled by one or more control wires (160). The control wires (160) also may have a releasable joint (162), desirably an electrolytically severable joint made in accord, for instance, with the Guglielmi et al patents discussed herein.

During delivery of the inventive aneurysm patch (150), the radially extending arms (154) lie generally against the delivery catheter (152). Upon deployment, the control wires are axially manipulated to extend the radially extending arms (154) into the second shape depicted in FIGS. 2A and 2B.

Each of the variations shown in FIGS. 1A and 1B and in FIGS. 2A and 2B provide a fairly smooth surface to the lumen of the patent vessel exterior to the target aneurysm.

The radially extending members (102) in FIGS. 1A and 1B and (154) in FIGS. 2A and 2B, are required to undertake massive changes in shape during deployment in the human body. To undertake such stress, it is usually preferable that the various subassembly elements be produced of a material such as a super-elastic alloy. Super-elastic or pseudoelastic shape recovery alloys are well known in this art. For instance, U.S. Pat. Nos. 3,174,851; 3,351,463; and 3,753,700 each describe one of the better known super-elastic alloys, known as nitinol. These alloys are characterized by their ability to be transformed from an austenitic crystal structure to a stress-induced martensitic (SIM) structure at certain temperatures and then to return elastically to the austenitic shape when the stress is removed. These alternating crystal structures provide the alloy with its super-elastic properties. The alloy mentioned in the three patents just above, is a nickel titanium alloy. It is readily commercially available and undergoes the austenitic-SIM-austenitic transformation at a variety of temperatures between −20° C. and +30° C.

These alloys are especially suitable because of their capacity to recover elastically, almost completely, to the initial configuration once the stress is removed. Typically in services such as are described here there is little permanent plastic deformation, even at relatively high strains. This ability allows the retainer device to undertake substantial bends both as it is collapsed to enter the various tubular delivery devices and as it undertakes further bending in passing through the vasculature. In spite of this bending, it returns to its original shape once the bend has been traversed without retaining kinks or permanent bends.

Of the super-elastic alloys currently available, we consider our preferred material to be nominally 50.6±2% nickel (atomic basis) with most of the remainder being titanium. Up to about 5% of the alloy may be a member of the iron group of metals, particularly chromium and iron. The alloy should not contain more than about 500 parts per million of oxygen, carbon, or nitrogen. The transition temperature of this material is not particularly important, but it should be reasonably below the typical temperature of the human body so to allow it to be in its austenitic phase during use. The diameter of the wires or ribbons making up the various array elements preferably are smaller than about 0.001 inches in diameter. These super-elastic alloys are not always completely visible under fluoroscopy as it is used in the human body. Consequently it may be desirable to add a covering of some kind to improve the radio-opacity of the device. Radio-opaque metals such as gold and platinum are well known. They may be added the various elements of this inventive device by such widely recognized methods as by plating or by wrapping the element in a radio-opaque wire or ribbon.

Although we have discussed producing these devices from super-elastic alloys, other metals may in certain circumstances be appropriate. Such metals include a number of the stainless steels and other highly elastic, if not super-elastic alloys. Furthermore, it is within the scope of this invention that the various array elements be of polymeric materials. Polymeric materials are somewhat easier to work with in forming a device. Such polymeric materials may include members from the group of polyethylene, polypropylene, polytetrafluoroethylene, various Nylons, and the like. These polymers are easily chosen by one having ordinary skill in this art for the purposes shown herein.

The various electrolytically severable joints (108 in FIGS. 1A and 1B and 162 in FIGS. 2A and 2B) may also be denominated as sacrificial links. The core wire (106) and control wires (160) are typically coated with an electrical insulator which is not susceptible to dissolution via the electrolysis process in blood or other ionic media. Suitable coatings include such insulating materials as the polyfluorocarbons (e.g., Teflon), polyurethane, polyethylene, polypropylene, polyimides, or other suitable well known polymeric materials. The various electrolytically severable joints are not coated with such an insulator but they are made of materials which are susceptible to electrolytic dissolution in blood. These electrolytically severable joints may be a simple uninsulated continuation of, e.g., the stainless steel core wire (106) which has been insulated proximally of the joint. It should also be apparent that the sacrificial joints are more susceptible to electrolysis than any of the other elements of the device near that joint. Further discussion of the construction of, placement of, and other physical details of such electrolytically severable joints may be found in U.S. Pat. No. 5,122,136 to Guglielmi et al.; U.S. Pat. No. 5,354,295 to Guglielmi et al.; and U.S. Pat. No. 5,624,449 to Pham et al.; and others.

Figure 3A:
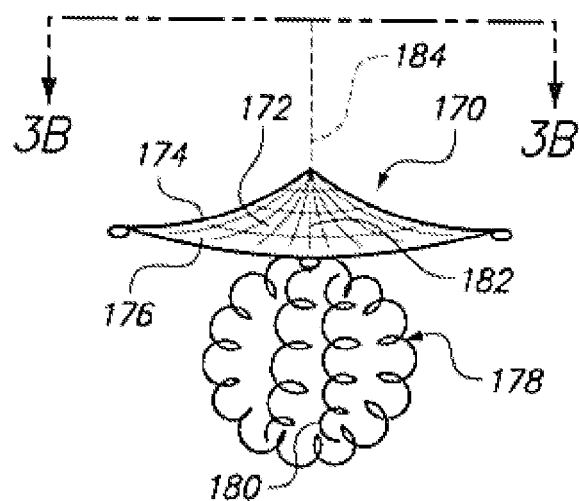
FIG. 3A shows side view of an aneurysm patch in combination with an "anchor" residable within an aneurysm.
Figure 3B:
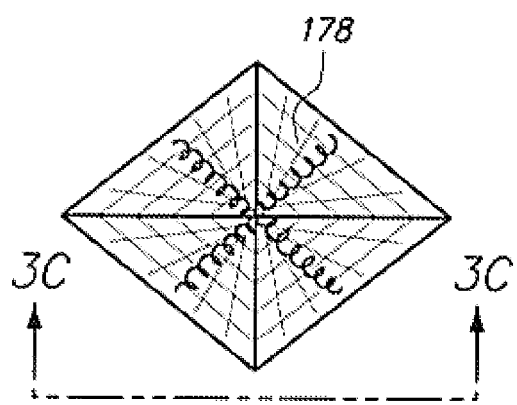
FIG. 3B shows an end view of the device depicted in FIG. 3A.
Figure 3C:
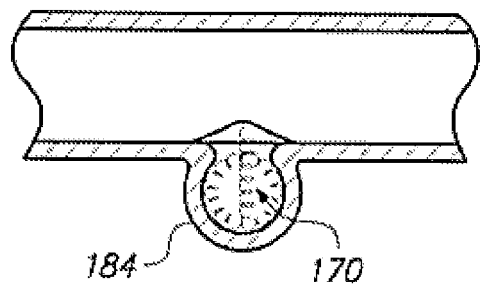
FIG. 3C shows the placement of the device depicted in FIG. 3A within an aneurysm.

The included fabric (104 and 156) may be a woven cloth, a flat woven mesh, a knitted mesh, or other common and non-critical sheetings. Although the radially extending arms (102 and 154) are preferably of a form which retains a large measure of elasticity after having been bent, the fabric material (104 and 156) need not be so elastic. Indeed it is preferable that the material making up sheeting (104 and 156) not have substantial strength so to allow the device to be folded and placed into the various delivery catheters and the like discussed above without adding unnecessary stiffness. The sole function of the fabric material (104 and 156) is simply to maintain the presence and stability of the vaso-occlusive coils in the aneurysm FIGS. 3A, 3B, and 3C show another variation of the inventive aneurysm closure assembly (170) having a patch portion (172) made up of a number of radially extending members (174) which are joined at their outer ends. The radially extending members (174) are also joined by a soft fabric (176) which again may be scrim-like. Completing the device is a soft cage (178) made up of a plurality of, e.g., platinum or nickel-titanium coils (180) or wires. A connector (182) connects the soft cage (178) and the patch portion (172) and is situated within the necknof the aneurysm after implantation. The radially extending members (154) are typically joined to a releasable joint (184), again desirably an electrolytically severable joint made in accord, for instance, with the Guglielmi et al patents discussed herein.

As may be seen from FIG. 3B, the cage subassembly (178) extends outwardly from the general center-line of the device and generally should be sized to conform to the size of, and generally to the shape of, the aneurysm.

FIG. 3C shows the general placement of the device within an aneurysm (184). The soft cage (178) is within the the sac of the aneurym (184) and the patch portion (172) is within the lumen of the artery.

Figure 4A:
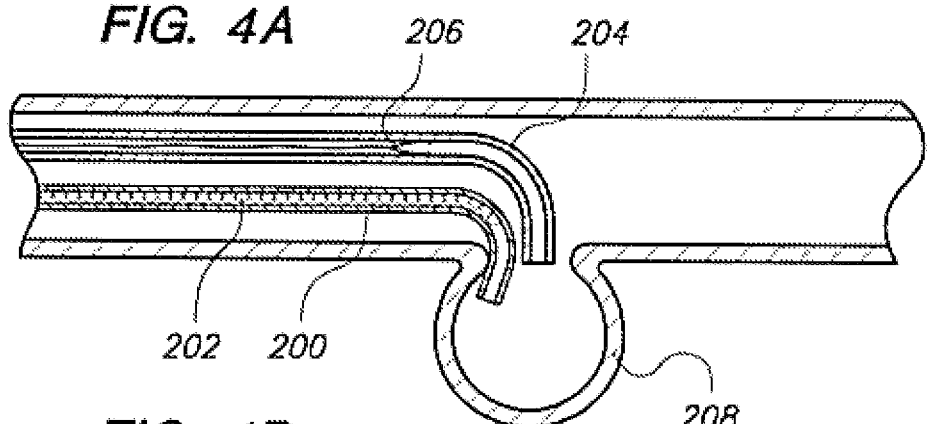
FIGS. 4A–4D show a generalized procedure for introducing the aneurysm patch shown in FIGS. 1A and 1B and its allied vaso-occlusive device into the target aneurysm.
Figure 4B:
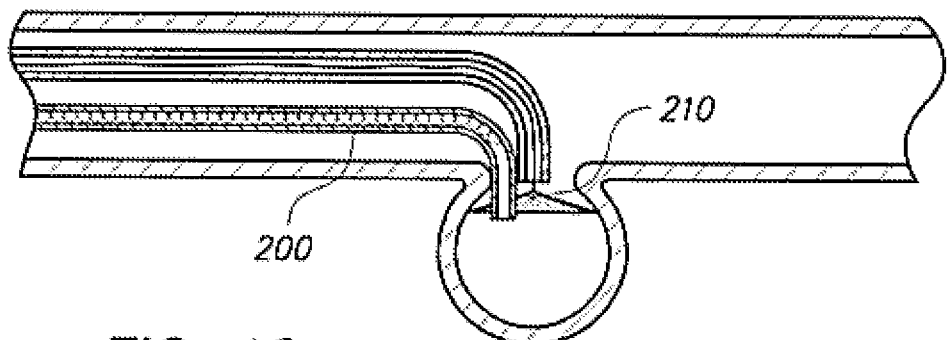

FIGS. 4A through 4D show the manner in which the devices found in FIGS. 1A and 1B are typically used in occluding and stabilizing an aneurysm. FIG. 4A shows the placement of the distal end of a catheter (200) carrying a vaso-occlusive device (here depicted to be a coil (202)) and a second catheter (204) carrying the aneurysm mouth patch (206) within the mouth of an aneurysm (208). FIG. 4B shows catheter (204) having been withdrawn proximally a bit and the aneurysm retainer device (206) positioned in the mouth of the aneurysm (208). Note that the aneurysm retainer device (206) is sufficiently flexible to distend around the coil delivery catheter (200).

Figure 4C:
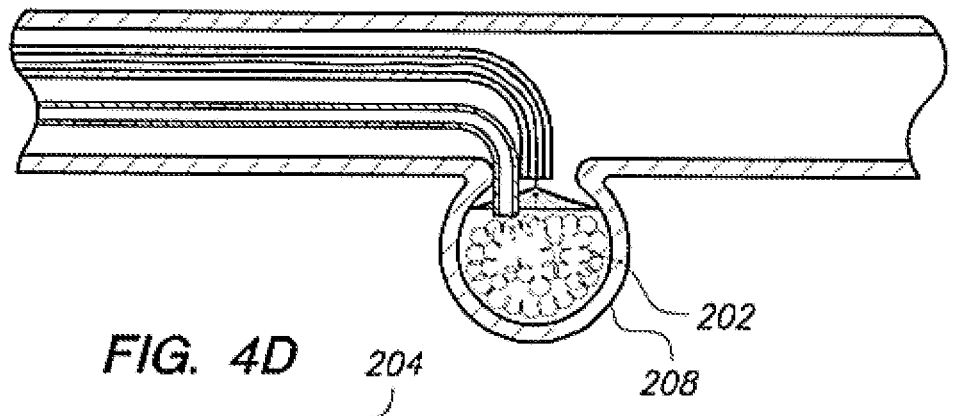

The aneurysm retainer device (206) is shown with its electrolytic joint (210) still intact. FIG. 4C shows the introduction of vaso-occlusive devices, in this case helically wound coils (202) into the vascular cavity interior to the aneurysm retainer device (206).

Figure 4D:
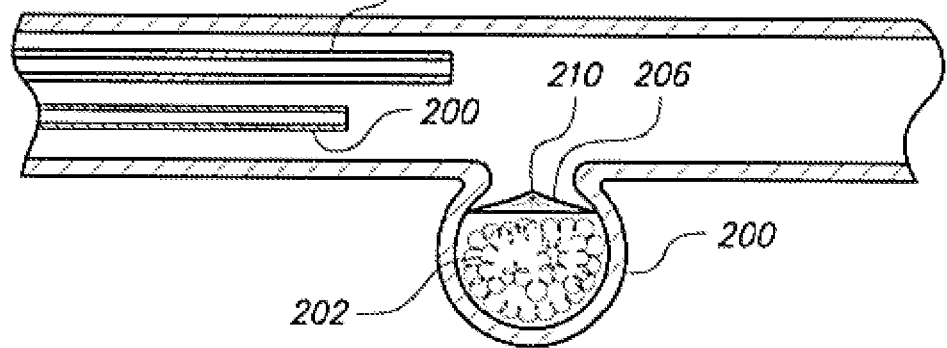

FIG. 4D shows the vascular cavity of aneurysm (206) filled with coils (202) and the electrolytic joint maintaining the continuity between the core wire (shown in other drawings) severed and both catheter (200) and catheter (204) have withdrawn leaving the vaso-occlusive device (202) in place within aneurysm (208). The aneurysm neck patch (206) is shown stabilizing the presence of that coil (202) and preventing that vaso-occlusive coil (202) from being drawn into the feed vessel.

Figure 5A:
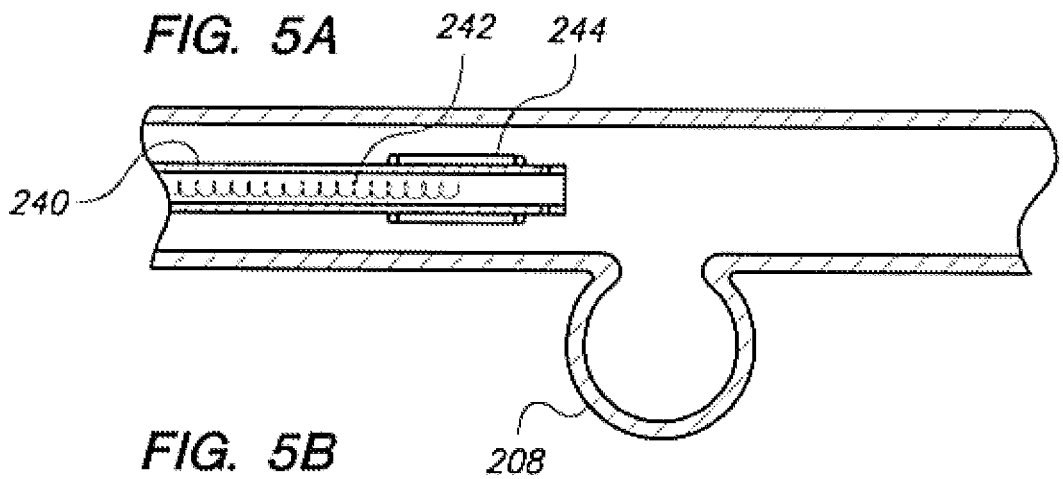
FIGS. 5A–5D show a generalized procedure for introducing the aneurysm patch shown in FIGS. 2A and 2B and its allied vaso-occlusive device into the target aneurysm.

FIGS. 5A through 5D show the manner in which the devices found in FIGS. 2A and 2B are typically used in occluding and stabilizing an aneurysm. FIG. 5A shows the placement of the distal end of a catheter (240) within the mouth of an aneurysm (208). Catheter (240) carries a vaso-occlusive device in its interior (here depicted to be a coil (242)) and an aneurysm neck patch (244) on its exterior.

Figure 5B:
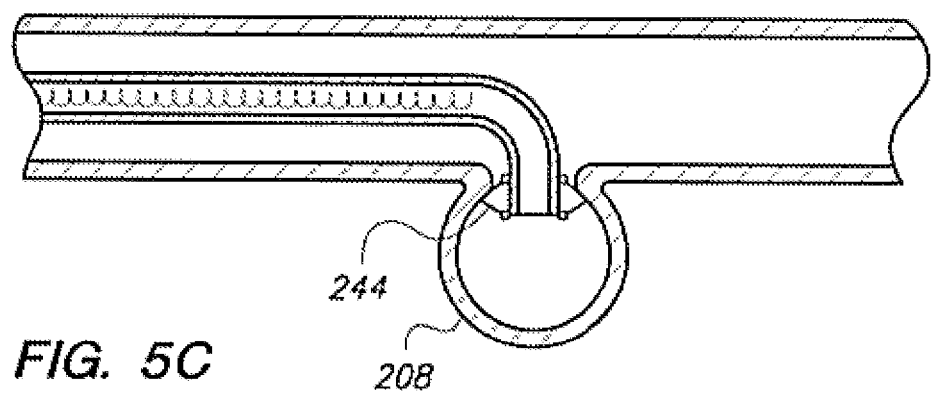

FIG. 5B shows catheter (240) and the aneurysm retainer device (244) positioned and expanded in the mouth of the aneurysm (208). Note that the distal end of catheter (240) is still within the aneurysm (208) even after the expansion of the aneurysm neck patch (244). The aneurysm retainer device (244) is shown with its electrolytic joint (210) still intact.

Figure 5C:
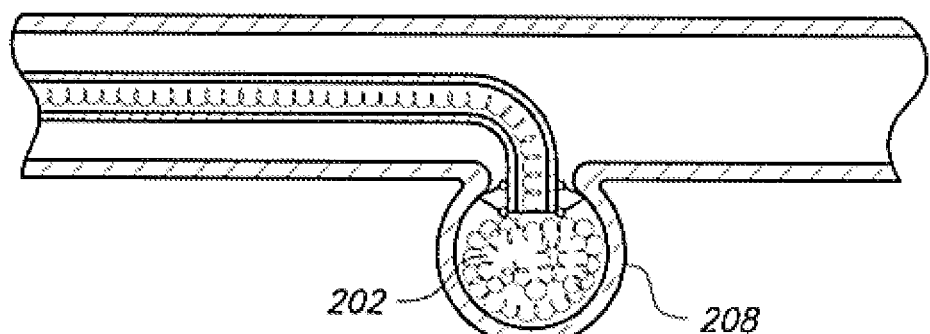

FIG. 5C shows the introduction of vaso-occlusive devices, e.g., helically wound coils (202) into the vascular cavity interior to the aneurysm retainer device (244).

Figure 5D:
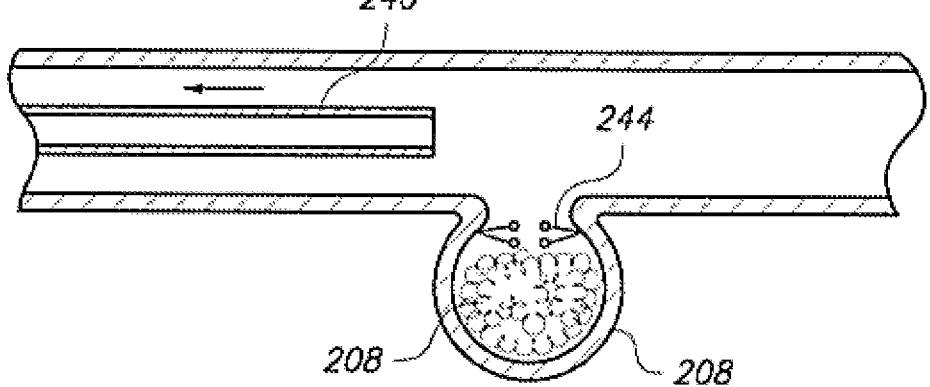

FIG. 5D shows the vascular cavity of aneurysm (208) filled with coils (202) and the electrolytic joint maintaining the continuity between the core wire (shown in other drawings) severed and catheter (240) withdrawn leaving the vaso-occlusive device (202) in place within aneurysm (208).

Many alterations and modifications may be made by those of ordinary skill in this art, without departing from the spirit and scope of this invention. The illustrated embodiments have been shown only for purposes of clarity and the examples should not be taken as limiting the invention as defined in the following claims. Which claims are intended to include all equivalents, whether now or later devised.

We claim as our invention:

1. An aneurysm retainer assembly deliverable through a vascular catheter, comprising:
   a vaso-occlusion device retainer subassembly comprising a junction region, a plurality of radially extending members, each member having a proximal end and a distal end, the respective proximal ends fixedly attached to said junction region, the respective distal ends configured for non-traumatic tissue contact in order to retain said retainer subassembly at a site in a body, and a fabric fixedly attached between ones of said plurality of members, said retainer subassembly having a first delivery shape during delivery and a second deployed shape, different than the first delivery shape, after said retainer subassembly is delivered to the site,
   an elongated delivery member, and
   an electrolytically severable joint which is integrally continuous between said retainer subassembly and said elongated delivery member, severable upon application of a suitable current to said joint.

2. The retainer assembly of claim 1 wherein said plurality of radially extending members are constructed of a material selected from the group consisting of stainless steels and super-elastic alloys.

3. The retainer assembly of claim 1 wherein said fabric is angiogenic.

4. The retainer assembly of claim 1 wherein the said plurality of radially extending members are radio-opaque.

5. The retainer assembly of claim 1, wherein said elongated delivery member is a core wire comprising at least one radio-opaque marker.

6. A retainer assembly deliverable through a vascular catheter comprising:
   a.) an elongated tubular delivery member having a proximal end and a distal end,
   b.) an electrolytically severable joint, a proximal end of which electrolytically severable joint being fixedly and integrally attached continuously to the distal end of said elongated tubular delivery member, and
   c.) a vaso-occlusive device retainer subassembly comprising a plurality of radially extending members detachably attached to a distal end of said electrolytically severable joint, said retainer subassembly having a first delivery shape when within said vascular catheter and a second deployed shape, different from the first delivery shape, a fabric fixedly attached to and between each of said plurality of radially extending elements, said electrolytically severable joint being severable upon application of a suitable current to said joint.

7. The retainer assembly of claim 6 wherein said plurality of radially extending members are constructed of a material selected from the group consisting of stainless steels and super-elastic alloys.

8. The retainer assembly of claim 6 wherein fabric comprises polyethylene terephthalate.

9. The retainer assembly of claim 6 wherein fabric further comprises collagen.

10. The retainer assembly of claim 6 wherein the said plurality of radially extending members are radio-opaque.

11. The retainer assembly of claim 6, wherein said elongated tubular delivery member additionally comprises at least one radio-opaque marker.

* * * * *